United States Patent
Hage

[19]

[11] Patent Number: 5,898,487
[45] Date of Patent: Apr. 27, 1999

[54] APPARATUS AND METHOD FOR DETERMINING THE CONCENTRATIONS OF HEMOGLOBIN DERIVATIVES

[75] Inventor: Roger Hage, Graz, Austria

[73] Assignee: AVL Medical Instruments AG, Schaffhausen, Switzerland

[21] Appl. No.: 08/822,733

[22] Filed: Mar. 24, 1997

[30] Foreign Application Priority Data

Apr. 2, 1996 [AT] Austria ........................... 591 96

[51] Int. Cl.⁶ ..................... G01N 33/48; A61B 5/00
[52] U.S. Cl. ..................... 356/39; 600/320; 600/322; 422/82.05; 436/66
[58] Field of Search ..................... 356/39; 600/320, 600/322; 422/68.1, 82.05, 82.09; 436/66

[56] References Cited

U.S. PATENT DOCUMENTS

| | | | |
|---|---|---|---|
| 5,331,958 | 7/1994 | Oppenheimer | 356/39 |
| 5,372,135 | 12/1994 | Mendelson et al. | 356/39 |
| 5,616,501 | 4/1997 | Rodriguez et al. | 356/39 |

FOREIGN PATENT DOCUMENTS 0575712 12/1993 European Pat. Off. .

OTHER PUBLICATIONS

International Publication No. WO 94/08237 to A.P. Shepherd et al., dated Apr. 14, 1994, entitled, "Method and Apparatus for Direct Spectrophotometric Measurements in Unaltered Whole Blood".

*Primary Examiner*—Robert H. Kim
*Assistant Examiner*—Zandra V. Smith
*Attorney, Agent, or Firm*—Watson Cole Grindle Watson, P.L.L.C.

[57] ABSTRACT

An apparatus for determining the concentrations of n hemoglobin derivatives in a sample of undiluted, unhemolyzed whole blood provided in a cuvette, employs a device producing a primary light beam formed of at least n substantially monochromatic, narrow-band components of different wavelengths. Further provided is a detection device for measuring of the radiation passing through the cuvette. At least two measuring geometries are provided for spectral detection of a collimated central beam and at least one scatter beam, and detection of the central beam departing from a first measuring location in the cuvette takes place in a first measuring position on the axis of the primary beam, and detection of the scatter beam takes place in a second measuring position if it departs from the first measuring location in the cuvette, or in the first measuring position if it departs from a second measuring location in the cuvette, whereby the axes of the central beam and the scatter beam(s) enclose angles $\alpha_i$, and the evaluation device includes a unit for calculating the concentrations of the n hemoglobin derivatives from the at least 2n measurement values obtained in the at least two measuring geometries and a predetermined calibration matrix.

6 Claims, 2 Drawing Sheets

APPARATUS AND METHOD FOR DETERMINING THE CONCENTRATIONS OF HEMOGLOBIN DERIVATIVES

BACKGROUND OF THE INVENTION

The present invention relates to an apparatus for determining the concentrations of n hemoglobin derivatives in a sample of undiluted, unhemolyzed whole blood provided in a cuvette, including a device to produce a collimated primary light beam with at least n substantially monochromatic, narrow-band components of different wavelengths, and a detection device for measurement of the radiation passing through the cuvette, as well as an evaluation device connected with the detection device.

DESCRIPTION OF THE PRIOR ART

Determination of the hemoglobin derivatives $O_2Hb$, RHb, COHb, MetHb, and/or SHb in hemolyzed blood, i.e. CO oximetry, is a known and reliable method which is based on transmission spectroscopy and Lambert Beer's law of absorption. The whole blood sample is hemolyzed either by ultrasound or chemical procedures in order to remove undesirable light scattering, before it is irradiated at several different wavelengths. The maximum possible number of hemoglobin derivatives to be determined corresponds to the number of different wavelengths used for excitation. Hemolyzed blood is a clear solution of different hemoglobin pigments ideally obeying Lambert Beer's law of absorption. The use of multicomponent analysis will permit calculation of the unknown concentrations.

Unhemolyzed whole blood on the other hand is a suspension of hemoglobin-containing red blood cells in plasma. The difference in the refractive indices of red blood cells and plasma is responsible for light scattering. As the dimension of the red blood cells (5 $\mu$m approx.) is greater by a factor 10 than the analytical wavelength (visible or near infrared light), Mie's Theory may be employed to treat scattering by a single blood cell. Since the light scatter is diffuse and the distances between the individual blood cells are small, complex multiple scatterings will result. Multiple absorptions of the scattered light are to be expected as a consequence. Another problem in unhemolyzed whole blood is presented by the sieving effect. The incident light travels along different optical paths. A part of the light beam impinges on blood cells and is attenuated (absorbed and/or scattered), another one passes through the sample unimpaired. Due to the above phenomena Lambert Beer's Law is invalidated, which theoretically applies only to collimated light in a continuous medium.

Other attempts have been concerned with finding a theoretical formula for the oxygen saturation of unhemolyzed whole blood in order to support empirical methods of pulse oximetry. Apart from oxygen saturation and hemoglobin content, however, it has not been possible to obtain additional parameters from the sum signal of transmitted light intensity.

In Applied Optics, Vol.27, 4027–4033 (1988, "Comparison of Mie Theory and light scattering of red blood cells"), angle-dependent distribution of light scattering in strongly diluted, unhemolyzed whole blood was compared with the results of exact Mie Theory. The results found in that paper cannot be transferred to undiluted, unhemolyzed whole blood, however, because of the occurrence of multiple scatterings which are negligible only in strongly diluted samples (2%).

It is to be expected that angle-dependent distribution of scattered light will depend on several factors, such as hematocrit (H), mean cellular hemoglobin content (MCHC), cell shape and cell orientation. Since these factors are unknown and inaccessible in conventional CO oximetry, reliable and accurate results are obtained with unhemolyzed whole blood only if (A) the influence of these factors is minimized, or (B) additional information is made available.

From International Publication Number WO 94/08237 an apparatus and method of the above type have become known which allow determination of the concentrations of various hemoglobin derivatives in whole blood without hemolysis or dilution. The apparatus includes a large-area detector to receive a maximum of the scattered light. The method employs a complicated iterative correction of scattering to eliminate from the sum signal measured the contributions of the scattered light, and to enable Lambert Beer's Law to be employed. The concentrations of the components of the whole blood sample being analysed are determined with the use of the intensities detected for each wavelength used, and of predetermined molar extinction coefficients for each of the components being analysed.

In EP-A2 0 575 712 a method and device are described for direct use in an in-vitro or extracorporeal blood circuit, with which hematocrit and another quantity, such as sodium concentration, are determined simultaneously. For this purpose two photodetectors are used, the first detector being positioned in the direction of the incident light (centrally located), and the second detector being positioned off the central direction, such that the signal detected by the second detector will vary strongly with sodium concentration. The measurement method utilizes the influence of sodium concentration, which affects cell shape and volume, on the geometry of the transmitted light pencil.

SUMMARY OF THE INVENTION

Departing from the state of the art described above, it is the object of the present invention to propose an apparatus and a method of simultaneously determining the concentrations of several hemoglobin derivatives in a sample of undiluted, unhemolyzed whole blood, where the need for complex iterative mathematical evaluation procedures is largely eliminated.

According to the invention this object is achieved by proposing that at least two measuring geometries be provided for spectral detection of a collimated central beam and at least one scatter beam, and that detection of the central beam departing from a first measuring location in the cuvette take place in a first measuring position on the axis of the primary beam, and that detection of the scatter beam take place in a second measuring position if it departs from the first measuring location in the cuvette, or in the first measuring position if it departs from a second measuring location in the cuvette, whereby the axes of the central beam and the scatter beam(s) enclose angles $\alpha_i$, and further that the evaluation device include a unit for calculating the concentrations of the n hemoglobin derivatives from the at least 2n measurement values obtained in the at least two measuring geometries and a predetermined calibration matrix. Depending on the respective measuring configuration and the number of different measuring positions or measuring locations the angles $\alpha_i$ may assume a variety of values, so long as separation between central beam and scatter beams is ensured.

The monochromatic light components of different wavelengths preferably penetrate the cuvette in temporal sequence such that detection of the measurement values is simplified. It is also possible, however, to radiate the monochromatic radiation components into the sample simultaneously, and to provide for spectral separation by the detector.

Unlike all prior art the present invention employs for the first time additional spectral information contained in the scattered light, to make the necessary corrections for the purpose of accurate CO oximetry in unhemolyzed whole blood by means of transmission spectroscopy in vitro. By using a predetermined calibration matrix, which may be obtained once and for all by measuring known whole blood samples, the concentrations of $O_2Hb$, RHb, COHb, MetHb and/or SHb may be determined in a single step without iterations and subsequent corrections.

In a first variant the apparatus of the invention is provided with an optical device, preferably a rotatable or slideable mirror in the path of the primary beam, the latter defining a first measuring location in the cuvette in a basic position of the optical device, and a second measuring location in the cuvette in at least one further position of the optical device, both measuring locations enclosing an angle $\alpha_i$ with respect to a single measuring position. In this variant only one detection device is required, information from the central beam and that from the at least one scatter beam being detected in temporal sequence. By stepwise shifting or rotating of the mirror, a series of different scatter angles $\alpha_i$ may be sampled in a simple manner.

It is proposed in a second variant of the invention that, departing from a single measuring location in the cuvette, in addition to a first measuring position with a first detection device there be provided at least one second measuring position at the angle $\alpha_i$ relative to the axis of the central beam, in which is located a further detection device, or into which the first detection device may be tilted.

The measuring method of the invention includes:

(a) irradiating the sample with a primary beam of at least n substantially monochromatic components of different wavelengths;

(b) detecting the radiation penetrating the sample in a first measuring position located in the axis of the primary beam or central beam, whereby a set of absorption values $A_0$ (lambda) is determined in the central beam;

(c) detecting the radiation penetrating the sample in at least one other measuring position located in the axis of a scatter beam, which encloses an angle $\alpha_i$ with the axis of the primary beam, whereby at least one more set of absorption values $A_{\alpha i}$ (lambda) is determined in the scattered radiation;

(d) calculating the concentrations of n hemoglobin derivatives as functions of absorption values $A_0$ (lambda), $A_{\alpha i}$ (lambda) and a predetermined calibration matrix K.

The additional data provided by the scatter component will supply information on the corpuscular properties of the red blood cells responsible for the lack of success of previous methods.

If unhemolyzed blood is irradiated with n substantially monochromatic, narrow-band radiation components of different wavelengths, and measurements are made in, say, two measuring positions, 2n signals are obtained, which will allow determination of a maximum of 2n unknowns. For example, with four components to be determined ($O_2Hb$, RHb, COHb, MetHb) and four wavelengths, the overdetermined equation system (eight equations) will permit four additional factors to be taken into account, such as mean cellular hemoglobin content, hematocrit, volume and shape of a red blood cell.

By one-time application of efficient, multivariate calibrating methods in the laboratory, in particular, Partial Least Square (PLS) and Principle Component Regression (PCR), a reliable, a priori calibration matrix may be determined, which may be used with each apparatus of the same construction type and constant optical characteristics. Such a calibration matrix allows for non-ideal conditions, such as deviations from the ideal bandwidth of the monochromatic radiation components, and non-ideal extinction coefficients.

Additional, simple calibration and correction steps may be performed with the use of clear and turbid control fluids, for example, to correct for the film thickness of the sample in the cuvette or for diverse manufacturing tolerances of the detection optics. The clear control fluid addresses exclusively the central measuring position. In this instance film thickness may be corrected by means of dye measurement, as Lambert Beer's Law is valid. At the same time secondary reflections reaching the sensitive light scatter detectors may be detected and corrected for.

With the turbid solution, a certain, defined angle distribution is to be expected. In this instance a standardization step could be performed, for example, using the ratio between scattered light and central light, to correct for sensitivity tolerances between the individual detectors.

Obviously, the new method is insensitive to the degree of hemolysis, so that it will supply accurate results even for 100% hemolyzed blood. In this instance the signal in the scatter position(s) would be zero, thus indicating an absence of scattering centers in the sample, and Lambert Beer's Law could be applied to the central signal only.

BRIEF DESCRIPTION OF THE DRAWINGS

The invention will now be further described with reference to the accompanying drawings, in which.

DETAILED DESCRIPTION OF PREFERRED EMBODIMENTS

Figure 1:
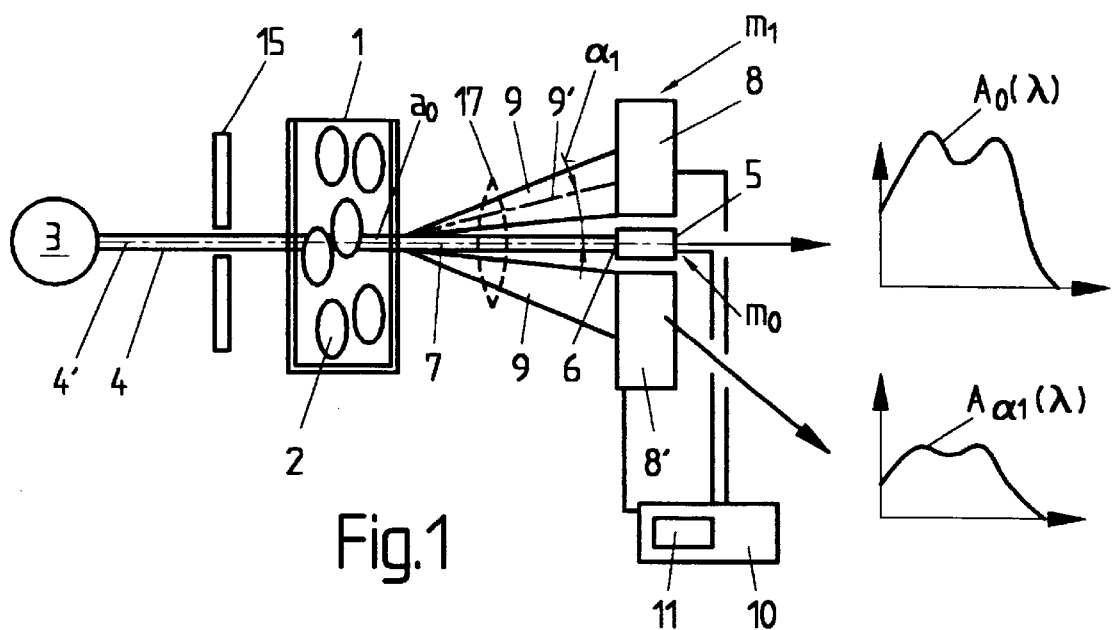
FIG. 1 is a schematical representation of an apparatus of the invention for determining the concentrations of several hemoglobin derivatives.

In the apparatus presented in FIG. 1, which is designed for determining the concentrations of n hemoglobin derivatives, a sample 2 of undiluted, unhemolyzed whole blood is contained in a cuvette 1. A device 3 provides a primary light beam 4 consisting of at least n monochromatic, narrow-band components of different wavelengths $lambda_i$. A first detection device 5 in a first measuring position $m_0$, which is located in the axis 4' of the primary beam 4 or the central beam 7, has a comparatively small beam entrance area 6, and is primarily used for measuring radiation from the central beam 7. In a second measuring position $m_1$, at an angle $\alpha_i$ relative to the axis 4' of the primary beam 4, is located a second detection device 8, which is used for detection of the scatter beam 9 in the axis 9'. Both detection devices 5 and 8 detect radiation from a measuring location $\alpha_0$, and are connected via signal leads to an evaluation device 10 provided with a unit 11 for calculating the concentrations of the n hemoglobin derivatives by means of a stored calibration matrix.

The narrow-band, monochromatic radiation components may be produced in different ways, for example, by spectrally splitting the radiation of a beam of white light with a diffraction grating or prism. It is also possible to filter broadband, monochromatic radiation via interference filters or to select individual emission lines of a spectral line lamp with the use of filters.

For the purpose of determining four hemoglobin derivatives the sample is irradiated with at least four narrow-band (bandwidth smaller than 5 nm, preferably 2 nm), monochromatic radiation components of different wavelengths. This will yield at least 2n=8 spectral signals: four signals of the first detection device 5 and four signals of the second detection device 8. The different monochromatic radiation components of the primary beam may pass the sample either in temporal sequence or simultaneously. Preference is given to the alternative of time-sequenced irradiation, as this will minimize measuring expense. For efficient utilization of statistical calibrating methods (PLS, PCR), the system must be strongly overdetermined, i.e., n significantly greater than four (for four unknowns). A preferred number of radiation components would be 66. Wavelengths may be chosen from the visible and near infrared spectrum (500 to 700 nm) as desired. Preference is given to the 66 wavelengths from 520–650 nm, with an interval of 2 nm, for example.

As shown in FIG. 1, the primary beam 4 may be collimated to about 2 mm by an aperture 15. The detection device 5 in the first measuring position $m_0$ covers a central beam range of 0–5°, i.e., preferably 0–3°, and the second detection device 8 in the second measuring position $m_1$ a radiation scatter range of 5–30°, i.e., preferably 5–15°. Another detector 8' may be located in a symmetrical scatter position. It would also be possible to use only one detection device and to tilt or shift it from measuring position $m_0$ to measuring position $m_1$.

For better separation of the collimated central beam 7 from the diffusely transmitted scatter beam 9, an optical device 17, preferably a lens or lens system, may be placed between cuvette 1 and detection devices 5 and 8.

Figure 2:
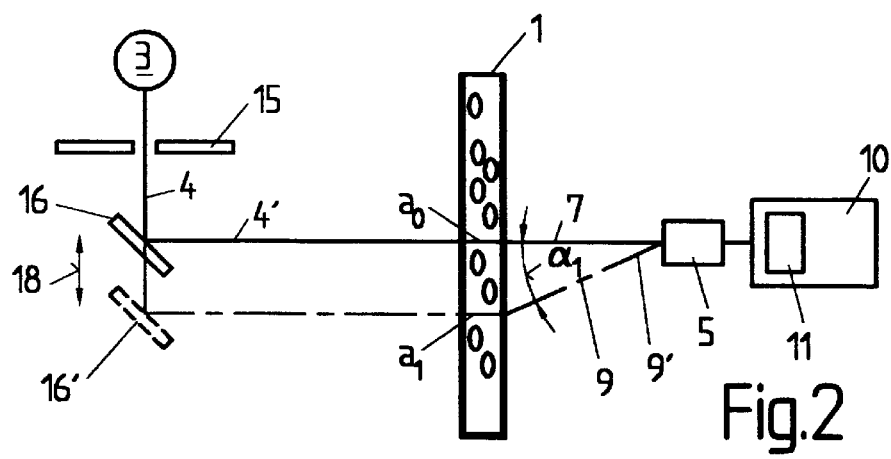
FIG. 2 presents an advantageous variant of the apparatus of the invention.

The embodiment presented in FIG. 2 obtains information from the scatter beam by shifting the axis 4' of the primary beam from a first measuring location $\alpha_0$ in the cuvette 1 into a second measuring location $\alpha_1$. This may be achieved by sliding an optical device 16, such as a mirror, along arrow 18 into a position 16'. With respect to measuring position $m_0$, the two measuring locations $\alpha_0$ and $\alpha_1$ form an angle $\alpha_1$ with the detection device 5. In order to produce additional measuring locations the mirror 16 could be shifted or rotated stepwise.

Figure 3:
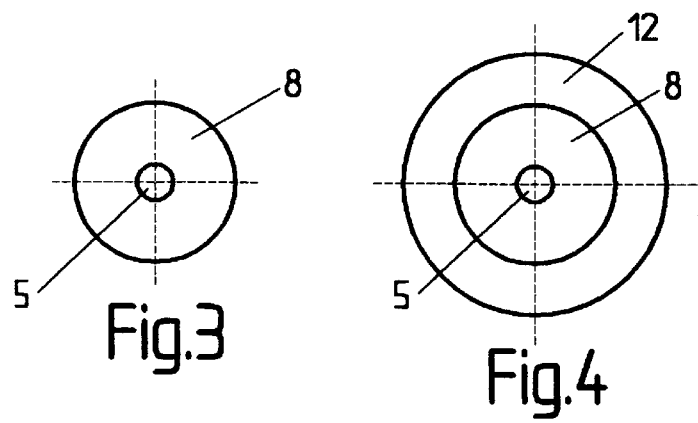
FIGS. 3–6 present variants of the detection device in an apparatus as shown in FIG. 1.
Figure 4:
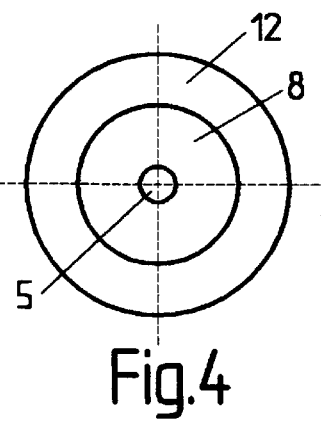
Figures 5, 6:
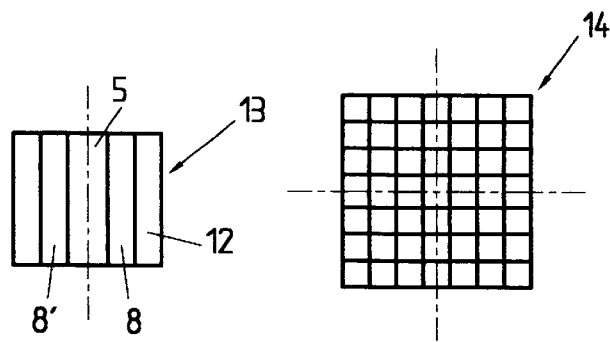

As is shown in FIGS. 3 and 4, detection devices 8 and 12 (FIG. 4) may be arranged in a circular ring around the centrally located first detection device 5. Apart from photodiodes, image-transmitting, optical fiber bundles may be employed. In a further variant a linear diode array 13 is used as shown in FIG. 5, or a CCD unit 14 as shown in FIG. 6.

Figure 7:
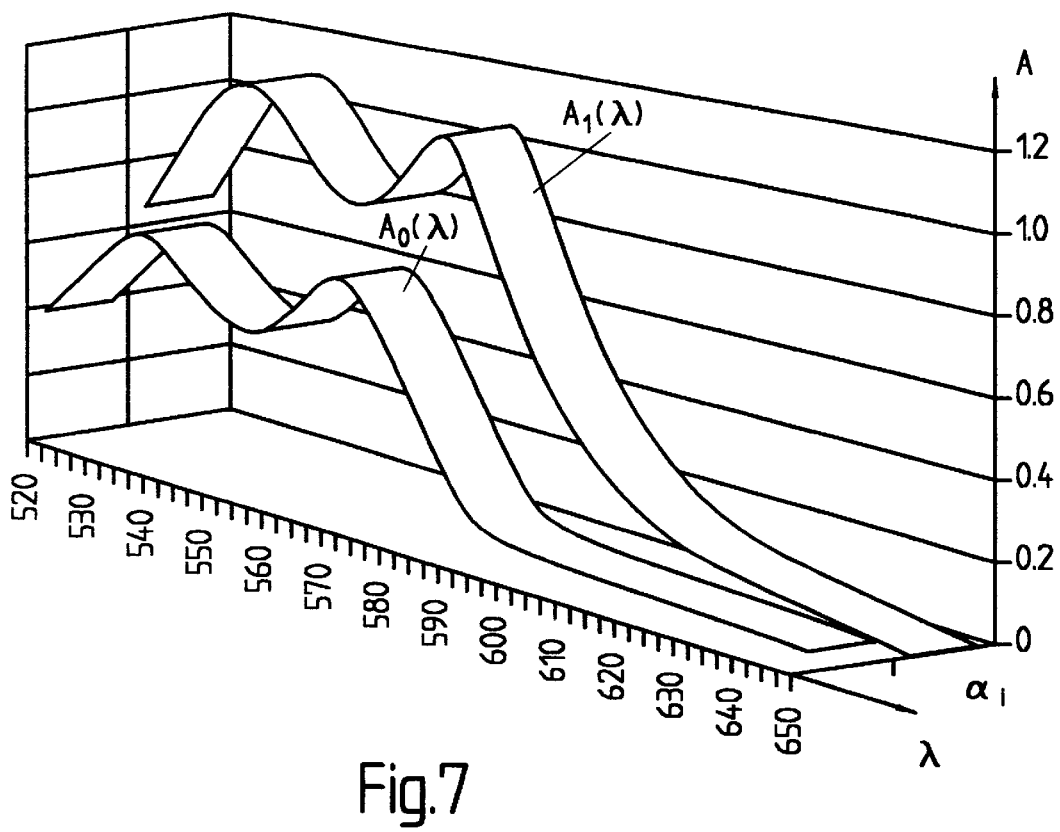
FIG. 7 presents absorption spectra measured with an apparatus as shown in FIG. 1.

FIG. 7 presents different absorption spectra for different measuring positions $\alpha_i$.

I claim:

1. An apparatus for determining the concentrations of n hemoglobin derivatives in an undiluted, unhemolyzed whole blood sample, comprising:

a cuvette for holding said sample, a device for directing a collimated primary beam into said sample, said primary beam having at least n substantially monochromatic, narrow-band radiation components of different wavelengths and defining a central axis, an optical device positioned in the central axis of said primary beam wherein in a basic position of said optical device, said primary beam defines a first measuring location in said cuvette, and in at least one further position of said optical device, said primary beam defines at least one second measuring location in said cuvette, said first and second measuring locations enclosing an angle $\alpha_i$ with respect to a single measuring position, a detection device for measuring radiation passing through said cuvette, and an evaluation device connected with said detection device, wherein at least two measuring geometries are provided for spectral detection of a collimated central beam and at least one scattered beam, wherein detection of said central beam departing from said first measuring location in said cuvette takes place in said first measuring position on said central axis of said primary beam, wherein detection of said scattered beam takes place in said first measuring position when departing from said second measuring location in said cuvette, whereby said central axis of said central beam and the axis of said at least one scattered beam enclose said angle $\alpha_i$, and further wherein said evaluation device includes a unit for calculating the concentrations of said n hemoglobin derivatives from at least 2n measurement values obtained in said at least two measuring geometries and from a predetermined calibration matrix.

2. Apparatus as claimed in claim 1, wherein an optical device is placed between said cuvette and said at least one detection device in order to separate said collimated central beam from said diffusely transmitted scattered beam.

3. An apparatus for determining the concentrations of n hemoglobin derivatives in an undiluted, unhemolyzed whole blood sample, comprising:

a cuvette for holding said sample, a device for directing a collimated primary beam into said samples said primary beam having at least n substantially monochromatic, narrow-band radiation components of different wavelengths and defining a central axis, a detection device for measuring radiation passing through said cuvette, and an evaluation device connected with said detection device, wherein at least two measuring geometries are provided for spectral detection of a collimated central beam and at least one scattered beam, wherein detection of said central beam departing from said first measuring location in said cuvette[0ax4]akes place in said first measuring position on said central axis of said primary beam, wherein detection of said scattered beam takes place in a second measuring position when departing from said first measuring location in said cuvette, whereby said central axis of said central beam and the axis of said at least one scattered beam enclose an angle $\alpha_i$, wherein, departing from a single measuring location in said cuvette, in addition to a first measuring position with a first detection device there is provided at least one second measuring position at said angle $\alpha_i$ relative to said central axis of said central beam, in which is located a further detection device, or into which second measuring position said first detection device is tilted, wherein said second detection device and further detection devices are arranged in a circular ring around said centrally located first detection device, and wherein said evaluation device includes a unit for calculating the concentrations of said n hemoglobin derivatives from at least 2n measurement values obtained in said at least two measuring geometries and from a predetermined calibration matrix.

4. Apparatus as claimed in claim 3, wherein said detection device in said first measuring position has a small beam entrance area covering a central beam range of 0–5° and said second detection device in said second measuring position detects a radiation scatter range which is adjacent to said central beam range.

5. Apparatus as claimed in claim 3, wherein said detection device in said first measuring position has a beam entrance area of 0–3°.

6. Apparatus as claimed in claim 3, wherein an optical device is placed between said cuvette and said at least one detection device in order to separate said collimated central beam from said diffusely transmitted scattered beam.

* * * * *